United States Patent [19]

Hansjurgens

[11] Patent Number: 5,573,552
[45] Date of Patent: Nov. 12, 1996

[54] ELECTROTHERAPEUTIC APPARATUS

[76] Inventor: Achim Hansjurgens, Rebbergweg 1, D-76229 Karlsruhe, Germany

[21] Appl. No.: 392,866
[22] PCT Filed: Aug. 26, 1993
[86] PCT No.: PCT/DE93/00789
    § 371 Date: Mar. 2, 1995
    § 102(e) Date: Mar. 2, 1995
[87] PCT Pub. No.: WO94/05370
    PCT Pub. Date: Mar. 17, 1994

[30] Foreign Application Priority Data

Sep. 5, 1992 [DE] Germany ............... 42 29 693.5

[51] Int. Cl.$^6$ ..................................... A61N 1/32
[52] U.S. Cl. ............................................ 607/68
[58] Field of Search ........................... 607/67, 68

[56] References Cited

U.S. PATENT DOCUMENTS

| | | |
|---|---|---|
| 3,774,620 | 11/1973 | Hansjurgens . |
| 5,018,524 | 5/1991 | Gu et al. . |
| 5,048,523 | 9/1991 | Yamasawa . |
| 5,109,847 | 5/1992 | Liss et al. ................... 607/68 |

FOREIGN PATENT DOCUMENTS

| | | |
|---|---|---|
| 296496 | 6/1971 | Austria . |
| 2545675 | 4/1976 | Germany . |
| 3010716 | 9/1981 | Germany . |
| 3335849 | 4/1985 | Germany . |
| 3541106 | 5/1987 | Germany . |

OTHER PUBLICATIONS

"Elektrische Differential–Therapie" (Electrical Differential Therapy), pp. 9, 49, 68–70, Hansjurgens et al, 1990.

"Fibel der Elektrodiagnostik und Elektrotherapie" (Primer of Electrodiagostics and Electrotherapy), p. 193, Herbert Edel, 1983.

Primary Examiner—William E. Kamm
Assistant Examiner—Scott M. Getzow
Attorney, Agent, or Firm—Baker & Daniels

[57] ABSTRACT

For an apparatus for electrotherapeutic applications operating in the medium-frequency range between 1000 Hz and 100,000 Hz where, in relation to a body part to be treated, a circuit with medium-frequency current (MF current) is applied across two electrodes, the invention proposes to keep the amplitude of the MF current constant and to modulate the frequency by one thousand to several thousand Hz (corner frequencies) with a modulation frequency of >0 to several hundred Hz (for instance 200 Hz) in order to generate in synchronism with the modulation frequency action potentials in the treatment area.

12 Claims, 5 Drawing Sheets

ELECTROTHERAPEUTIC APPARATUS

The present invention relates to an apparatus for electrotherapeutic applications which operates in the medium frequency range between 1000 Hz and 100,000 Hz, with paired, diametrically opposed electrodes applied in relation to a body part to be treated.

Figure 12:
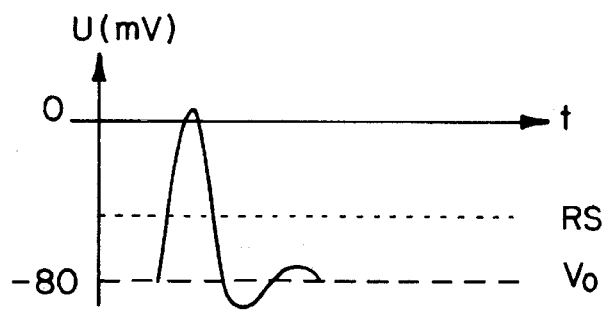

It has been known long since and so far also been utilized electrotherapeutically to force excitable cells (nerves, muscles and receptors of nerve ends) of the human body, by electrical stimuli externally supplied in the form of electrical pulses, to an electrical response, the so-called action potentials (refer to FIG. 12). These action potentials are cell-intrinsic electrical pulses with a defined height and width for the relevant cell type. For one nerve, for instance, a pulse width of about 1 ms and a height of about 80 mV to 100 mV is typical. The cell reverts to its cell membrane voltage, which at rest, depending on cell type, has a value between 60 mV and 120 mV. This voltage is caused by different ion concentrations in the extracellular and intracellular spaces separated by the cell membrane. More positive ions are found outside the cell. According to definition, the potential outside the cell is set to 0 V, so that a negative potential is given in the cell (refer to FIG. 12).

In healthy humans, the action potentials are generated by the body itself and utilized for information transfer and to trigger cellular processes.

In electrotherapy, therapeutic effects are induced by specific generation of action potentials (defined number and at specific loci).

Prior apparatuses for electrotherapy use a plurality of different current, or pulse shapes. Aiming to choose the electrotherapy best suited for the present (specific) indication, the therapist should be able to revert to criteria of maximally clear definition. These criteria derive from the replies to questions about the effectiveness and tolerance of the various current forms.

The spectrum of effects includes, e.g., the areas of pain alleviation, stimulation of striated and nonstriated muscles, of influencing perfusion, the detumescent mechanisms, of the areas of checking inflammatory processes and of promoting regeneration (wounds, accelerated healing of bones, etc.). The aim in the application should always be achieving the desired effect in the affected area by proper selection of the current form, either distal or proximal to the electrode or in the depth of the body.

Regarding tolerance, it should be assured that the current will not cause any damage, neither systemically nor locally.

The systemic tolerance of currents is determined primarily by the ventricular fibrillation threshold and the risk of triggering epileptic seizures. This means that the therapeutic range should be removed as far as possible from these thresholds. Thus, currents are to be preferred in which these thresholds are especially high.

The local tolerance is determined by the risk of burns and cauterizations as well as by the pain threshold.

Therefore, preference goes to currents and pulse shapes with which the desired effects are obtained, without any negative side effects being felt by the patient.

Basically, prior electrotherapeutic apparatuses are based on two stimulus current methods, the polarity-dependent "polar stimulation principle" and the polarity-independent "apolar stimulation principle."

Low-frequency currents (LF current) ranging from 0 to 200 Hz are used in the "polar stimulation principle." Hyperpolarization (rise in membrane voltage) occurs beneath the positive electrode, the anode, making the spacing between the potential in the cell and the stimulus threshold greater. In contrast, the membrane voltage drops beneath the negative electrode, the cathode. As the stimulus threshold is reached, the cell triggers automatically an action potential.

Prior stimulant current apparatuses employ different pulse shapes in the low-frequency spectrum of about >0 to 200 Hz (LF current). Applicable are, e.g., the so-called delta currents, rectangular currents, diadynamic currents, high-voltage currents, ultrastimulant currents, faraday currents—to name but a few. Some currents have a direct current component, which additionally backs the polar effects.

There are two frequency-dependent methods of using action potentials therapeutically:

Functional imitation principle:
  The number of action potentials generated by the excitable cell (nerve or muscle) for the performance of its tasks is ascertained. In therapy, the same number of pulses are then generated in the relevant cell by stimulation, thereby backing the cell in performing its tasks.
  For instance, a stimulation frequency of up to 6 Hz is applied to generate up to 6 individual contractions per second.

Fatigue principle:
  In contrast, when forcing the cell (nerve or muscle) to generate action potentials, by stimulation at elevated frequency and appreciably more often than the cell would be required to do so to perform its tasks, it fatigues after a short time. The opposite effect occurs. The cell fatigue can be explained by energy-consuming processes in the formation of action potentials.
  For instance, a sclerosed muscle can be relaxed according to this fatigue principle by stimulating it with a "high" frequency of, e.g., 100 Hz or 200 Hz.

To generate any action potentials at all, of course, the intensity must be chosen sufficiently high to exceed the stimulus threshold. The level of intensity to be set depends on the following factors:

the position (depth) of the cell to be stimulated in the tissue (distance from the electrode), the size of the electrodes and the tissue resistances in the region penetrated by the current, which, in turn, are influenced by the parameters of the current form.

In practice, current form and electrode size are prescribed. To stimulate now a group of cells at a certain distance from the electrode (for example, deep in the tissue), the intensity continues to be increased until action potentials occur. A possible disadvantage of this is that cells which are located between the region to be stimulated and the electrode and do not possess higher stimulus thresholds will be stimulated already at lower intensities.

Also with cells possessing higher stimulus thresholds, the intensity of the current pulses is in practice "simply" raised (which on account of stressing the skin is not always possible).

As the intensity increases, cells located deeper and deeper, or cells ever more distal from the electrodes, are being stimulated successively. With the apolar stimulation principle, only so-called medium-frequency alternating currents (MF currents) without any direct current component are employed. Meant by MF currents are sinusoidal alternating currents with a frequency of >1000 Hz to 100,000 Hz. A single cycle (alternating pulse) has with sufficient intensity a polar effect. An alternating current resulting from polar, as such subliminal short alternating pulses (MF pulse) is able to trigger an action potential in a nerve or muscle cell.

A "summation effect" occurs. At increasing frequency, ever higher intensities are needed too, in order to be able to trigger action potentials in the cells. WYSS has proved beyond doubt that the generation of action potentials with MF pulses proceeds entirely independently of polar effects. This means that wherever the intensity and number of oscillations is sufficiently large, action potentials will be generated irrespective of the momentary polarity of the MF current (WYSS, Oscar A.M.: Prinzipien der elektrischen Reizung [Principle of Electrical Stimulation], NEUJAHRS-BLATT, published by the Natural Research Society in Zurich for the year 1976, Kommissionsverlag Leeman AG, Zurich, 1976, 28–34).

MF pulses are applied at a low-frequency rhythm of >0 to about 200 Hz and MF carrier frequencies of >1000 Hz to 100,000 Hz. In practice, this is mostly a sinusoidal, amplitude-modulated MF current (AM-MF current). The following principles are in agreement with those described in conjunction with the "polar stimulation principle."

Functional imitation principle:
    In synchronism with the MF pulses (AM frequency), action potentials occur in excitable cells. The cell is thereby induced to exercise its natural functions, which emanate from this frequency.

Fatigue principle:
    To fatigue excitable cells, MF pulses with elevated amplitude-modulated frequencies are used.

As the current intensity rises, cells are stimulated successively that are located deeper and deeper (more distal from the electrodes).

Along with an increasing MF carrier frequency, ever more intensity is needed to generate action potentials (WYSS, loc.cit., 41–43, FIG. 17/p. 41, FIG. 18/p. 42). The illustrations were taken from the booklet titled "Prinzipien der elektrischen Reizung" [Principles of Electrical Stimulation] with the kind permission by Prof. Dr. Oscar A.M. WYSS. FIG. 17 and 18 show the dependence of the stimulus threshold on medium-frequency pulses as a function of the carrier frequency.

On the basis of the medium-frequency alternating current, the following additional options of therapy are given:

When stimulating with (constant-amplitude) MF current of sufficient intensity, an action potential is generated first. With MF current that flows for a longer time, the decaying flank of the action potential remains at the depolarization level (permanent depolarization), which amounts to about one-half of equilibrium potential. Upon shutting the MF current off, the membrane voltage drops then, delayed, to the level of equilibrium potential (WYSS, loc.cit., FIG. 13/p. 36). The following subitems describe the therapeutic utilization of the permanent depolarization.

Blocking

Pain alleviation and influencing perfusion
    High intensities which, depending on the properties of the region being treated, range at the tolerance limit cause a blocking of nerve transmission paths, due to the permanent depolarization. This genuine nerve block (proof established by BOWMAN, Bruce R., 1981, dissertation E. K. University of LJubljana, Rancho Los Amigos Hospital, Downey, Calif., U.S.A.) is utilized, e.g., for pain blocking in phantom-limb pains or for stellatum block in blood flow disorders.

Muscular Contraction

Muscle training in voluntary innervation insufficiency and muscle distention
    With the nerve muscle apparatus intact, the striated muscle (skeletal muscle) is stimulated directly by permanent depolarization. This results in muscle contraction, which is used, e.g., in voluntary innervation insufficiency of the muscles or to stretch the antagonists of spastic muscles. During treatment, the intensity should be interrupted by pauses in short intervals. The intensity also may be increased and decreased between 100% and about 50% of the adjusted value.

Generating strong muscle contraction forces
    Very strong muscle contractions may be induced without fatigue phenomena. In tetanic contraction, which can be induced with stimulation current of about 50 Hz and up, a rapid decrease of the muscle contraction force occurs contrarily, due to fatigue of the myokinetic units.

Cell Division

Wound healing and accelerated bone healing
    Permanent depolarization induces cell division in healthy cells. Wound healing may be promoted thereby, bone healing accelerated in fractures.

Moreover, MF currents induce under the effect of the electrical alternating field reciprocal movement (shaking effect) of charged molecules in the current-penetrated tissue, accompanied by rotation movements of the charged molecule shares. Achieved thereby is a greater probability of a "correct" meeting position of enzyme and substrate, which in metabolic processes interact chemically (metabolic facilitation). This shaking effect tends to level differences in concentration, in that diffusion processes which on account of existing concentration gradients proceed in certain directions are accelerated due to the kinetic energy that is additionally imparted (MF iontophoresis, inhibition of inflammation, alleviation of pain).

The shaking effect is especially effective at high intensities.

Distribution of inflammatory and pain mediators

Inhibition of inflammation and alleviation of pain
    In painful, inflammatory processes a high concentration of inflammatory and pain mediators is regularly found in the diseased tissue. This high concentration is reduced (dispersed) by the shaking effect. Caused by high current intensities, the "shaking intensity"—the same as the frequency - is of great significance for the therapeutic effects (HANS-JÜRGENS, MAY, Elektrische Differential-Therapie [Electrical Differential Therapy], Karlsruhe 1990).

Influencing of metabolism (diffusion, mitochondria, cyclic AMP)

Facilitation and promotion of metabolic processes
As described above, the biochemical metabolic processes are facilitated.

Also in penetrating cell cultures with MF current it has been found that the number of mitochondria ("energy plants" of the cells) and their size increase significantly (KOMITOWSKI and EHEMANN 1990, internal note).

An important messenger substance of the cell, the cyclic AMP, can also be influenced in its concentration by MF current, with dependence of MF intensity existing (DERTINGER, 1989, Kernforschungszentrum Karlsruhe, NAGY Nemectron GmbH Karlsruhe).

Furthermore, a painless and strong muscle contraction can be induced with MF currents.

The so-called "threshold dissociation" occurs from 8 kHz, that is, the threshold amperage for muscle contraction goes below that of the sensible threshold (EDEL, H.: Fibel der Elektrodiagnostik und Elektrotherapie [Primer of Electrodiagnostics and Electrotherapy], Müller & Steinicke München 1983, p. 193). Strong muscle contractions can be induced without pain. Viewed therapeutically, threshold dissociation is of particular interest in utilizing the reversible process of muscle contraction, which is caused by the permanent depolarization of the MF current.

Due to the high intensities of the MF current, heat is generated in the current-penetrated tissue. But a prerequisite is that the patient not be discomforted by exceeding the thresholds (sensation, muscle, tolerance, pain).

Analogous to the improvement of the metabolic processes, also an iontophoresis can be accomplished with MF current, i.e., the administration of medications with the aid of current through the skin into the body. Owing to the physical circumstances, iontophoresis with MF current requires a longer treatment time and higher intensities as compared to galvanic current.

As described above and found insofar also in the pertaining trade literature (refer to book "EDIT®—Elektrische Differential-Therapie" [Electrical Differential Therapy] by A. HANSJÜORGENS and H. U. MAY, ©1990, Nemectron GmbH, Karlsruhe), the prior electrotherapeutic apparatuses employ, depending on diagnosis, low-frequency currents or amplitude-modulated medium-frequency currents at frequencies >0 to 200 Hz or medium-frequency currents at a frequency of >1000 Hz to 100,000 Hz, each with constant amplitude (intensity).

The problem underlying the present invention consists in providing an electrotherapeutic apparatus of the categorial type with which similarly and insofar synergistically the therapeutic effects achievable with low-frequency and medium-frequency current are obtained.

This problem is inventionally solved in that the operating frequency is frequency-modulated in a frequency band of up to several kHz with a periodicity in the low-frequency range of >0 to about 200 Hz.

Expressed in words other than used in the claim, the technical teaching of the inventional electrotherapeutic apparatus is to select a medium-frequency current corresponding to the medical diagnosis and the conjugate electrotherapy and to periodically vary the frequency of the medium-frequency current in a frequency band of, e.g., 2000 Hz with a modulation frequency of >0 to 200 Hz, that is, with a frequency of the LF currents. The apparatus according to the invention operates thus in accordance with the laws of frequency modulation (and not in accordance with the laws of amplitude modulation as known from the prior art).

The MF currents with constant amplitude (intensity) are thus used to generate action potentials in the low-frequency rhythm (LFR). In contrast, the intensity of the stimulant current is in all prior stimulus current methods for generation of action potentials increased and decreased in the low-frequency rhythm (LFR>0 to about 200 Hz). The intensity level of the relevant pulses, (LF pulse or enveloping curve of the MF pulse) depends on the stimulus threshold of the cell to be stimulated and the distance of the cell from the electrode. With cells seated deeper, a higher intensity is needed in order to compensate for the voltage drop that occurs in the tissue between electrode and cells to be stimulated. The stimulus threshold curve is traversed in each pulse at rising and diminishing intensity (vertically).

The electrophysiological background of the inventional teaching is as follows:

The dependence of the stimulus threshold upon the intensity and frequency has already been described. The higher the frequency of the current, the greater needs to be its intensity to surmount the stimulus threshold. These linearly ascending curves of electrophysiological thresholds now can be exceeded or gone below not only by variation of the current intensity, but also by variation of the frequency.

Exclusively MF currents are used now in the inventional method of frequency modulation. Once adjusted to the desired value, the intensity is kept constant during treatment. The carrier frequency of the constant-amplitude MF current is modulated in the low-frequency rhythm (FM-MF current), the curve of the stimulus threshold being traversed horizontally at diminishing and again rising frequency. Synchronous with the low-frequency rhythm, action potentials are generated.

Developments and special embodiments of the inventional basic principle are the object of the subclaims.

Figure 1A:
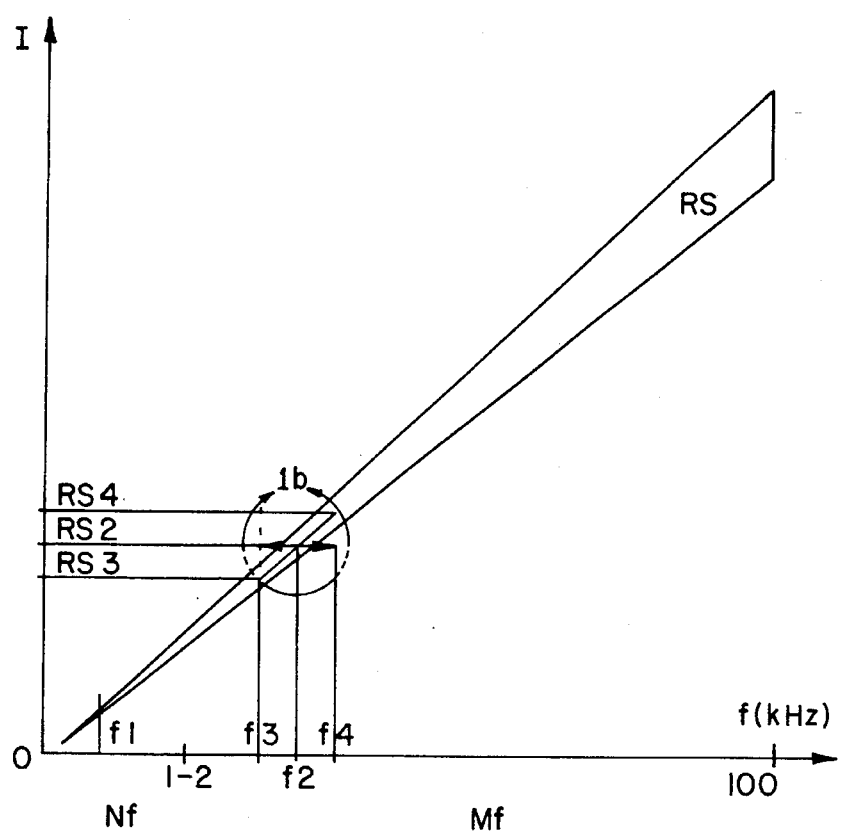
Figure 1B:
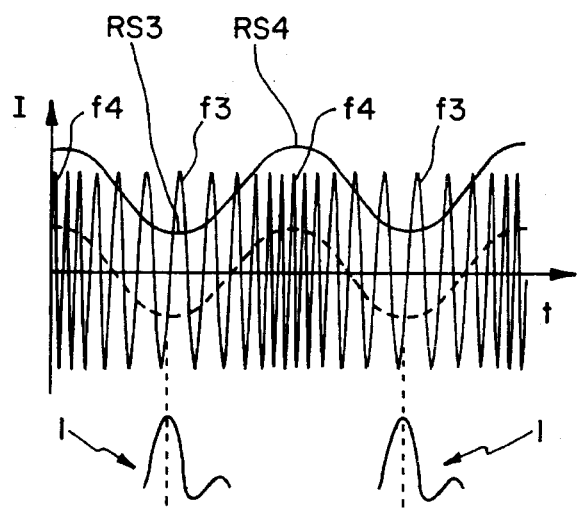
Figure 2:
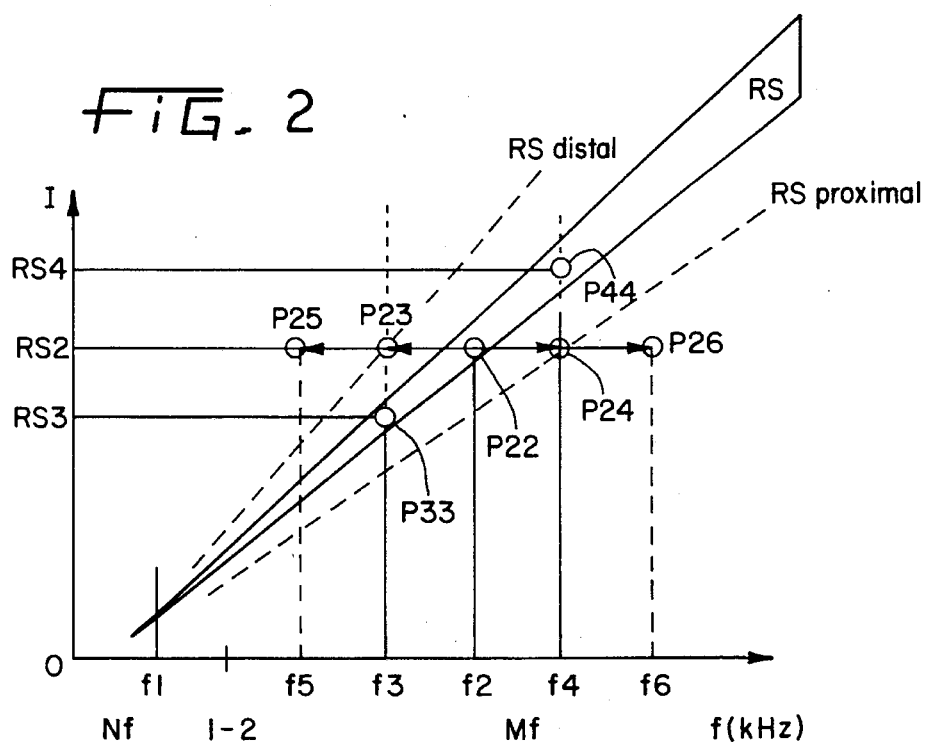
Figure 3:
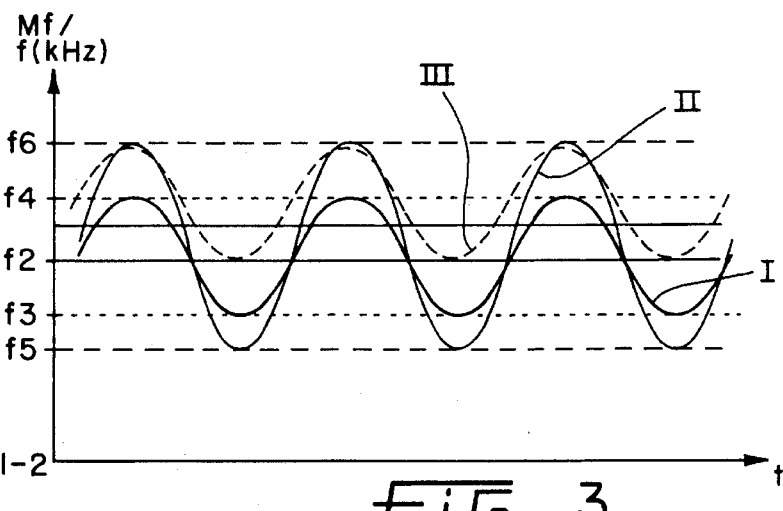
Figure 4:
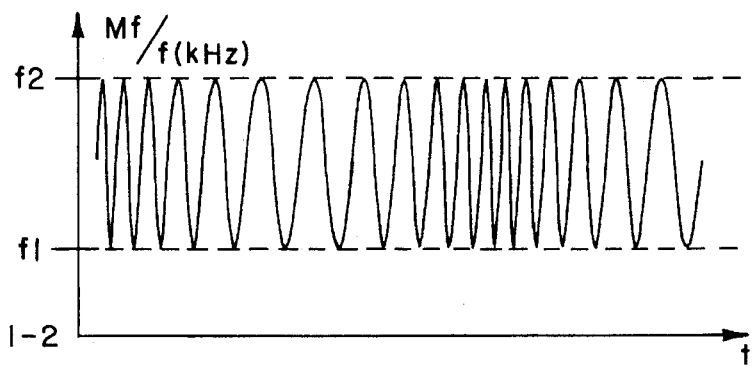
Figure 5:
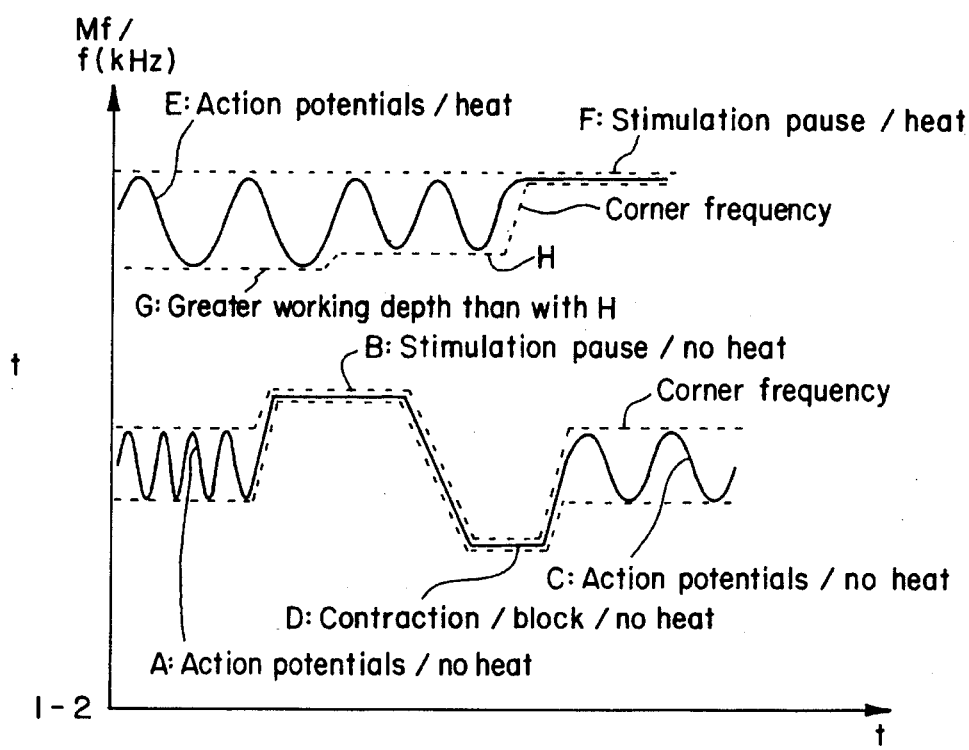
Figure 6:
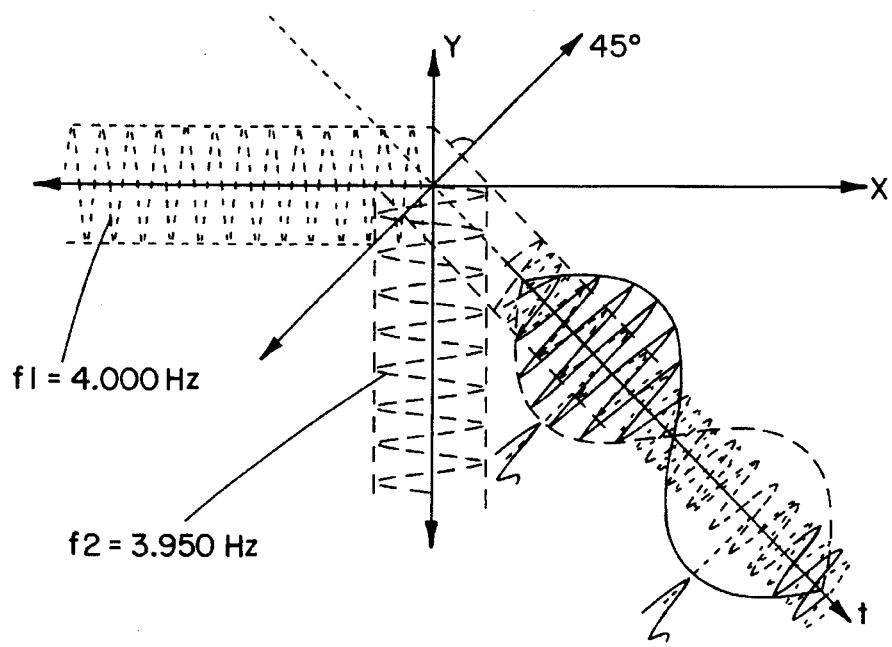
Figure 7:
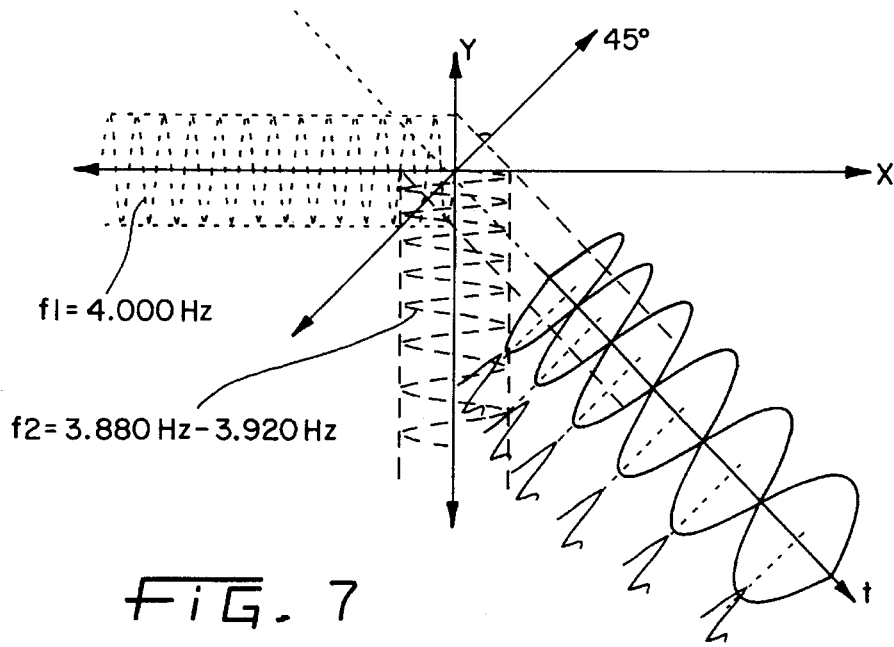
Figure 8:
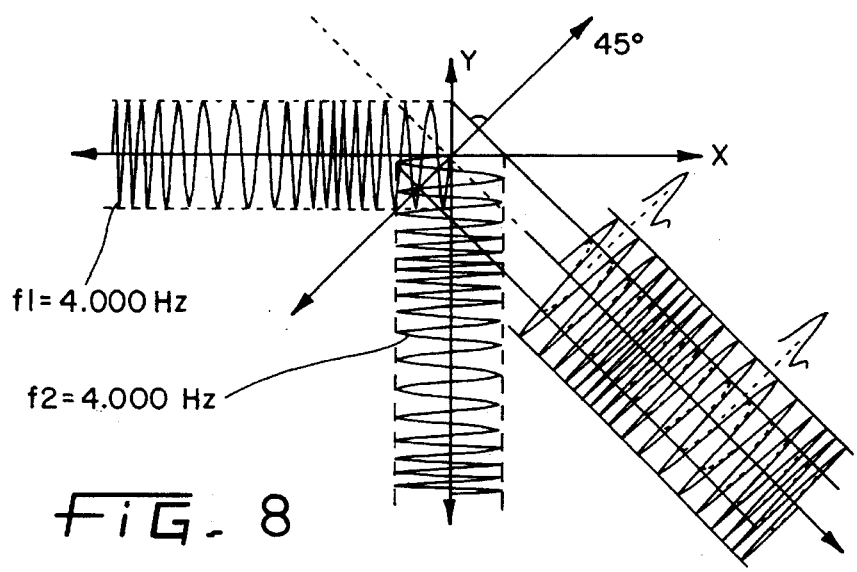
Figure 9:
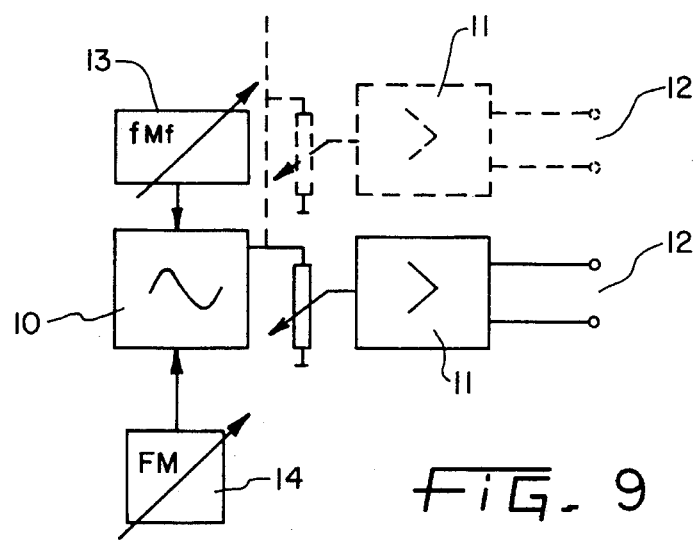
Figure 10:
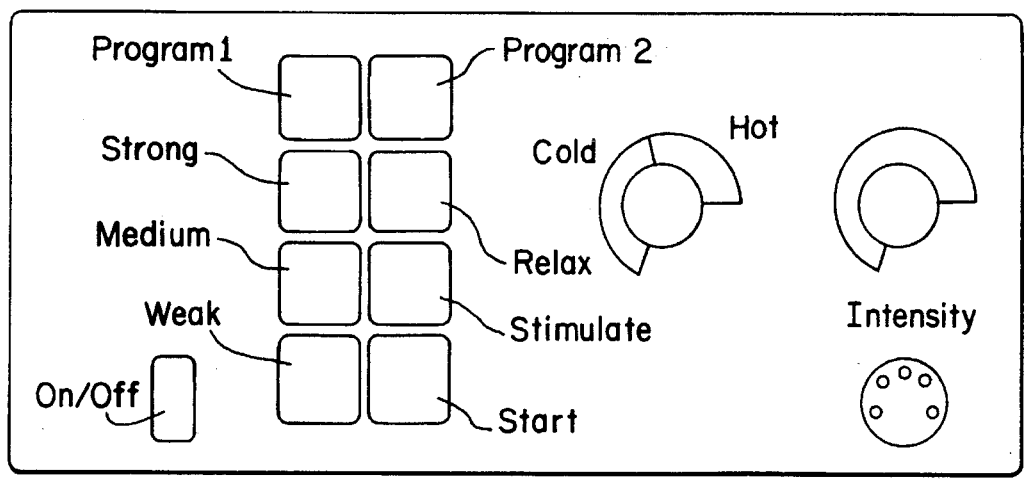
Figure 11:
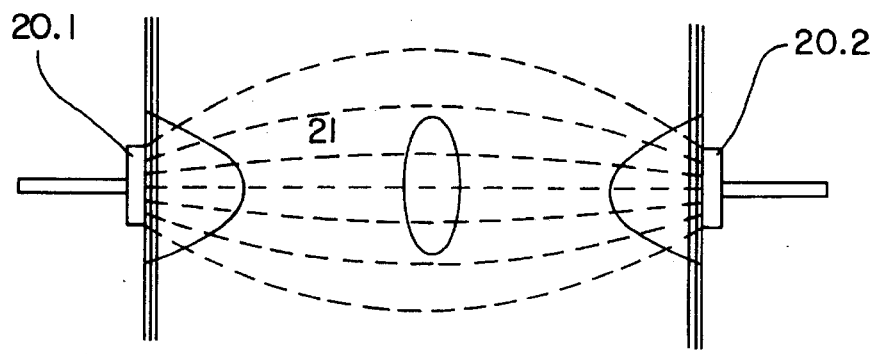

Details are more fully explained hereafter with the aid of the drawings; these show in FIG. 1, a basic illustration of the stimulation with frequency-modulated medium-frequency current;

FIG. 2, a section of FIG. 1 illustrating a frequency window in the current-frequency diagram;

FIG. 3, the section relative to FIG. 2 in the frequency-time diagram;

FIG. 4, an illustration of frequency-modulated medium-frequency current;

FIG. 5, a variation of the frequency window according to FIG. 3;

FIG. 6, a basic illustration of the stimulation (interference) with amplitude-modulated medium-frequency current;

FIG. 7, an illustration relative to FIG. 6 with variable stimulation frequency;

FIG. 8, an illustration relative to FIG. 1 with two superposed frequency-modulated medium-frequency currents;

FIG. 9, a block diagram of an inventional apparatus;

FIG. 10, an operating panel of the apparatus relative to FIG. 9;

FIG. 11, a two-pole electrode system;

FIG. 12, an action potential.

FIG. 1 shows in the current(I)-frequency(f) diagram the known illustration of a stimulus threshold RS with the fluctuation range diverging from the low-frequency range (refer to WYSS, loc.cit., FIG. 18).

In FIG. 1, the frequency of the MF current is modulated in the low frequency rhythm (LFR) between values f3 (lowest frequency) and f4 (highest frequency). f3 and f4 shall be termed corner frequencies of the resulting frequency window.

The area of the entire frequency window is depicted, enlarged, in the upper part of FIG. 1, but with the frequency-modulated medium-frequency current as well the stimulus threshold and the frequency modulation curve (MF curve) being illustrated in time the frequency of the FM curve is set at f1, has thus a value from the low-frequency range. An example of a frequency-modulated FM curve is illustrated in FIG. 4.

For f1=2 Hz, for example, two action potentials 1 are generated per second, since the stimulus threshold RS3 is reliably exceeded each time the frequency f3 with the adjusted intensity of the MF current is reached. Kept constant, the intensity of the MF current is at the time of f4 no longer sufficient to reach the stimulus threshold RS4.

To be able to generate action potentials with frequency-modulated medium-frequency currents at the low-frequency rhythm, the following interdependent parameters must be set correctly:

the carrier frequency of the medium-frequency current, the amplitude of the medium-frequency current, the modulation frequency and the corner frequencies of the frequency modulation (frequency window).

The carrier frequency of the medium-frequency current is selected depending on the relevant therapeutic requirements, which in the application of frequency-modulated medium-frequency currents allow both the utilization of action potentials and the effect of the medium-frequency current. Thus, the following effects of the medium-frequency current can be utilized simultaneously with those of the action potentials: generation of heat, medium-frequency iontophoresis as well as strong or lesser inflammatory inhibition, alleviation of pain and influencing of metabolic processes.

The intensity of the medium-frequency current (constant amplitude) to be adjusted derives from the frequency. The intensity is so selected that the threshold will not be exceeded yet.

The frequency of the frequency modulation is then adjusted according to therapeutic principles of functional imitation or fatigue.

Lastly, the corner frequencies of the frequency window are selected, that is, the frequencies between which the carrier frequency is supposed to vary at the low-frequency rhythm. The frequency window needs to be selected at least sufficiently large to allow reliably a horizontal exceeding of the threshold curve in the range of the preset carrier frequency. The frequency needed for that purpose is the low-frequency limit (f3 and point P23 in FIG. 2) of the frequency window; the upper frequency limit is the selected carrier frequency (f4 and point P24 in FIG. 2).

The advantages of this method illustrated with the aid of FIG. 1 (with FIG. 2 / FIG. 3) are that simultaneous therapeutic effects of action potentials and effects of the medium-frequency current (shaking effect) are possible with and without generation of heat.

All of the additional therapeutic options available with constant-amplitude medium-frequency current (CA-MF current) an be utilized simultaneously with the therapeutic effect of the action potentials and heat generated by frequency-modulated medium-frequency current, and at that, for instance for pain therapy with and without heat.

Furthermore, new therapy combinations with and without heat are possible, and at that, new combinations of the effects of medium-frequency current (permanent depolarization and shaking effect) and the action potentials generated by frequency-modulated medium-frequency currents can be applied in one and the same treatment by time and intensity variation of the frequency modulation curves (refer to FIG. 5, farther down).

The permanent depolarization is used:

to block cellular information—for instance pain block in phantom-limb pains and for stellatum block in perfusion disturbances, and in healthy cells for cell division—for instance in the treatment of wounds and fractures.

The shaking effect is used:

for distribution of pain mediators, for distribution of inflammatory mediators, for concentration-leveling processes between cells, for influencing metabolic processes and for iontophoresis with medium-frequency currents.

The muscular structure is favored, and at that, with simultaneous shaking effects, without therapeutically usable generation of heat. The frequency f is in the lower medium-frequency range, so that the required intensity of the medium-frequency current does not generate heat yet.

With reference to FIG. 2 it is noted yet that the following effects can be obtained by intensity variation of the frequency modulation curve:

to generate slow waves of contraction (covering myokinetic units seated deep and less deep) the frequency f of the frequency-modulated currents can be continually varied in several seconds from f5 (point P25) to f3 (point P23) and back again to f5.

to generate longer treatment phases between action potentials during which the cell can recover and only the shaking effect is generated, the frequency f of the medium-frequency currents can be varied from f3 (point P23) to f6 (point P26), and not only from f3 (point P23) to f4 (point P24), such as necessary for generation of action potentials.

FIG. 3 shows several frequency modulation curves in which both the working frequency f (refer to FM curves I+II versus III) and the corner frequencies (refer to FM curve I with II) are varied. The variation of the corner frequencies has the effects described in FIG. 2, while the variation of the working frequency by the higher current intensity (refer to FIG. 2, point P24, versus point P44 at F4) generates additionally heat.

The muscle structure is additionally promoted by the simultaneous generation of heat, by selecting a higher working frequency f of the medium-frequency.

The inventional application of constant-amplitude medium-frequency currents results in further electrophysiologically induced advantages of this method in the stimulation:

no low-frequency irritation of the skin by intensity variations of the stimulation current, thus painless application;

bundled penetration of the flux lines perpendicularly to the skin layers, thereby only slight energy losses of the current in surmounting the skin barrier and high stimulant effect subcutaneously and in depth;

utilization of the low skin resistances of the medium-frequency current (skin resistance diminishing with increasing frequency), thus painless application and only slight energy losses of the current in surmounting the skin barrier;

receding sensation of current after a few minutes of treatment, due to permanent depolarization of the medium-frequency current.

FIG. 5 is to show how, for instance by time variations of the frequency modulation curve, the following effects can be produced successively ($f_{FM-K}$ means here a selective fixed frequency):

tetanic contractions ($f_{FM-K} > 20$ Hz), pause ($f_{FM-K} = 0$, f MF=upper corner frequency), contraction (f of medium-frequency=lower corner frequency), pause ($f_{FM-K} = 0$, f of medium-frequency=upper corner frequency) and again tetanic contractions ($f_{FM-K} > 20$ Hz) etc.

Shown in the upper part of FIG. 5 is a frequency-modulated curve varied between the corner frequencies f3 and f4. Action potentials are generated in the curve range E, and a heat effect is produced simultaneously. The corner frequency f3 is after a preset time period varied insofar as—in keeping with the curve H varied as compared to G—the working depth is reduced. In the further time progression, only heat continues to be produced with constant current (refer to F).

Another treatment curve is shown in the lower part of FIG. 5. To begin with, an FM curve with the corner frequencies f1 and f2 is adjusted, which generates action potentials; due to the lower frequencies—unlike in the upper curve—no heat is generated (refer to A). The frequency modulation curve is followed by a stimulation pause (refer to B), and at that, in keeping with a level above the corner frequency f2; the required amperage is insufficient for generation of heat. Thereafter, to induce a contraction and/or block, a current with a frequency lower than the lower corner frequency f1 is applied (refer to D). Next, action potentials are generated again (refer to C), and at that, as well without generation of heat.

The generation of action potentials due to the inventionally frequency-modulated working frequency was shown with the aid of FIG. 1 . . . 5. FIG. 6, 7 and 8 are to portray advancements in the sense that two medium-frequency currents are superposed (interference method), resulting in amplitude modulation (AM) in the superposition field of the two medium-frequency currents.

Generated are amplitude-modulated currents, the exact processes being shown in FIG. 6 and 7. Amplitude modulation occurs due to the frequency difference of the two medium-frequency currents. One of the currents has a fixed medium-frequency, for instance of 4000 Hz, the other circuit carries a fixed frequency allowing selection, for instance, between 3800 Hz and 4000 Hz. Interference occurs in the areas in which the two currents superpose. When the circuit with the selective frequency has a frequency of, e.g., 3950 Hz, an amplitude-modulated medium-frequency current is produced whose amplitude is modulated by 50 Hz (refer to FIG. 6). Additionally, ranges between 3800 Hz and 4000 Hz can be modulated with a very slow frequency <0 to about 0.1 Hz. But this is done not for purposes of generating action potentials and should not be confused with the frequency modulation according to the present invention. After all, neither the modulation frequency between <0 to 200 Hz nor the frequency window of 200 Hz is sufficient to generate any action potential at all.

FIG. 7 shows an example of a frequency modulation of $1/15$ Hz and a frequency range of 80 Hz to 120 Hz. Hence, there are 80 action potentials generated which in 15 seconds continually increment to 120.

The amplitude modulation in the interference method occurs in the two directions of the 45°-line and with a phase shift of 90° in both directions, characterized by a line perpendicular to the 45°-line (refer to FIG. 5, 6, dashed line).

FIG. 8 shows the resulting current of a frequency-modulated medium-frequency stimulation with superposed currents. The objective of such super-position of two or more circuits is to increase the intensity in the superposition area (treatment area) by addition of the individual intensities, to a degree such that action potentials and the generation of heat will be induced here.

With the phase difference between the two currents =0, an intensity increase occurs only in the directions of the 45°-line (refer to FIG. 8). But when rotating the phase at a periodicity of >0 to about 0.1 Hz by 180°, the intensity increase alternates in the 45°-directions and in the two directions perpendicular to the 45°-line (refer to FIG. 8, dashed line).

Also, the frequencies of the two currents may have different values, so that, as shown in FIG. 6 and 7, amplitude modulation occurs in the superposition area. Slow frequency modulation of the inventional frequency-modulated medium-frequency stimulation induces at f3 (refer FIG. 1) action potentials due to amplitude modulation, and at f4 there continues to be effective only the medium-frequency shaking effect and, as the case may be, heat.

FIG. 9 shows a block diagram of an electrotherapeutic apparatus operating according to the invention, for one and also for two circuits.

The electrotherapeutic apparatus illustrated in FIG. 9 is basically comprised of an oscillator 10 with one (or several) amplifier(s) 11 coupled to it in parallel wiring. Coordinated with each amplifier 11 is a patient hookup 12 with the aid of which—diametrically opposed—electrode leads can be applied on the body part to be treated. Oscillator 10 is connected to a frequency generator 13 that determines the actual working frequency $f_{Mf}$; coordinated with the oscillator 10, additionally, is a frequency modulator 14 by which the working frequency $f_{Mf}$ is modulated within the preset corner frequencies.

FIG. 10 shows an operating panel of an inventional electrotherapeutic apparatus, depicting said apparatus as one which by means of buttons can be operated in simple fashion and as a portable apparatus for home use also by laymen. Depending on therapy, the various amperages and frequencies can be selected, and it is equally conceivable to connect this apparatus to a control module (microprocessor) which initiates specific treatment programs in keeping with the options presented in conjunction with FIG. 5.

FIG. 11 illustrates a two-pole electrode setup as an applicational example of an electrotherapeutic apparatus that operates according to the explained prescriptions and constraints.

To enable achieving the intended effect in the proximity of the electrodes 20.1, 20.2, a sufficient current density, i.e., the amperage per unit of area, needs to be assured in the treatment area 21. This is accomplished in accordance with the illustrated setup with a circuit closed across the two electrodes and through the treatment area. The greatest current densities and therapeutic effects associated with them occur always in electrode proximity, that is, in the treatment area (refer to stippled areas in FIG. 11).

With the treatment area located deep, four electrodes—refer to FIG. 6, 7 and 8—that is, two circuits, are applied in a fashion such that a superposition field will occur in the depth of the tissue, in the treatment area. The intensity is specifically increased in this area by addition of the intensities of both current circuits.

I claim:

1. An apparatus for electrotherapeutic applications operating in a medium-frequency range between 1000 Hz and 100,000 Hz comprising;

a circuit capable of generating a medium-frequency current of constant amplitude;

a modulator operatively coupled to said circuit and capable of frequency modulating the medium frequency output of said circuit;

two electrodes operatively coupled to said circuit to receive the modulated output of said circuit, the modulated output having a modulation interval of one thousand to several thousand Hz (corner frequencies) with a modulation frequency of >0 to several hundred Hz (for instance 200 Hz) in order to generate in synchronism with the modulation frequency action potentials in the treatment area.

2. Electrotherapeutic apparatus according to claim 1, characterized in that said circuit is capable of adjusting the frequency of the medium-frequency current to a level such that through the elevated intensity necessary for obtaining a stimulus threshold an additional generation of heat is induced.

3. Electrotherapeutic apparatus according to claim 2, characterized in that said modulation frequency and/or said modulation frequency, viewed over the treatment time, are variable.

4. Electrotherapeutic apparatus according to claim 2, characterized in that said modulation frequency is in a range of >0 to about 0.1 Hz.

5. Electrotherapeutic apparatus according to claim 2, characterized in that a plurality of said circuits are applied by way of two electrodes each, in such a way that the currents intersect in the treatment area, the frequency of the currents being equal or differing by an amount between >0 to about 200 Hz.

6. Electrotherapeutic apparatus according to claim 1, characterized in that said modulation interval and/or said modulation frequency, viewed over the treatment time, are variable.

7. Electrotherapeutic apparatus according to claim 6, characterized in that said modulation frequency is in a range of >0 to about 0.1 Hz.

8. Electrotherapeutic apparatus according to claim 6, characterized in that a plurality of said circuits are applied by way of two electrodes each, in such a way that the currents intersect in the treatment area, the frequency of the currents being equal or differing by an amount between >0 to about 200 Hz.

9. Electrotherapeutic apparatus according to claim 1, characterized in that said modulation frequency is modulated in a range of >0 to about 0.1 Hz.

10. Electrotherapeutic apparatus according to claim 9, characterized in that a plurality of said circuits are applied by way of two electrodes each, in such a way that the currents intersect in the treatment area, the frequency of the currents being equal or differing by an amount between >0 to about 200 Hz.

11. Electrotherapeutic apparatus according to claim 1, characterized in that a plurality of said circuits are applied by way of two electrodes each, in such a way that the currents intersect in the treatment area, the frequency of the currents being equal or differing by an amount between >0 to about 200 Hz.

12. Electrotherapeutic apparatus according to claim 5, characterized in that a phase difference with a constant value or modulated in the range of >0 to about 0.1 Hz exists between the two currents.

* * * * *

UNITED STATES PATENT AND TRADEMARK OFFICE
CERTIFICATE OF CORRECTION

PATENT NO. : 5,573,552
DATED : NOVEMBER 12, 1996
INVENTOR(S) : ACHIM HANSJURGENS

It is certified that error appears in the above-indentified patent and that said Letters Patent is hereby corrected as shown below:

Claim 3, column 11, line 6, delete "frequency" and substitute therefor --interval--

Claim 9, column 12, lines 6 and 7, delete "modulated".

Signed and Sealed this

Twenty-fifth Day of March, 1997

Attest:

BRUCE LEHMAN

*Attesting Officer*  Commissioner of Patents and Trademarks